(12) United States Patent
Gebreselassie et al.

(10) Patent No.: US 6,379,654 B1
(45) Date of Patent: Apr. 30, 2002

(54) ORAL COMPOSITION PROVIDING ENHANCED TOOTH STAIN REMOVAL

(75) Inventors: Petros Gebreselassie, Piscataway; Diego Hoic, Highland Park; James G. Masters, Ringoes; Michael Prencipe, West Windsor, all of NJ (US)

(73) Assignee: Colgate Palmolive Company, New York, NY (US)

( * ) Notice: Subject to any disclaimer, the term of this patent is extended or adjusted under 35 U.S.C. 154(b) by 43 days.

(21) Appl. No.: 09/698,453

(22) Filed: Oct. 27, 2000

(51) Int. Cl.[7] .............................. A61K 7/28; A61K 7/16; A61K 7/18; A61K 38/43
(52) U.S. Cl. .............................. 424/50; 424/49; 424/52; 424/94.1; 424/94.6; 424/94.63
(58) Field of Search ...................... 424/50, 52; 106/492; 514/23

(56) References Cited

U.S. PATENT DOCUMENTS

| | | | | |
|---|---|---|---|---|
| 5,624,906 A | * | 4/1997 | Vermeer et al. | 514/23 |
| 5,647,903 A | * | 7/1997 | McGill et al. | 106/492 |
| 5,817,297 A | * | 10/1998 | Ha et al. | 424/58 |

* cited by examiner

Primary Examiner—Christopher R. Tate
Assistant Examiner—Randall Winston
(74) Attorney, Agent, or Firm—Paul Shapiro

(57) ABSTRACT

An abrasive dentifrice composition which effects enhanced tooth and stain removal which comprises an orally acceptable vehicle containing a combination of a low oil absorption silica abrasive having an oil absorption value of less than 100 cc/100 g silica and an proteolytic enzyme.

14 Claims, No Drawings

ORAL COMPOSITION PROVIDING ENHANCED TOOTH STAIN REMOVAL

BACKGROUND OF THE INVENTION

1. Field of the Invention

This invention relates generally to oral compositions for removing tooth stains, and more particularly, to enzyme enhanced silica abrasive containing dental compositions effecting stain removal from teeth.

2. The Prior Art

Many substances that a person confronts or comes in contact with on a daily basis can "stain" one's teeth. In particular, foods, and fluids such as tea and coffee that one consumes tend to stain one's teeth. These products or substances tend to accumulate on the enamel layer of the tooth and form a pellicle film over the teeth. These staining and discoloring substances can then permeate the enamel layer. This problem occurs gradually over many years, but imparts a noticeable discoloration of the enamel of one's teeth.

Synthetically produced silicas incorporated in dentifrice compositions act as an abrasive to debride and physically scrub the external surface of the teeth. This scrubbing action removes the organic film (i.e. the pellicle), formed of salivary proteins which covers the teeth and which become stained and discolored. Such physical removal of the stained pellicle is a simple and effective means of removing the undesirable surface staining and discoloration which occurs daily.

Synthetic silicas useful as dentifrice abrasives include both silica gels and precipitated silicas which are prepared by the neutralization of aqueous silicate solutions with a strong mineral acid. In the preparation of silica gel, a silica hydrogel is formed which is then typically washed to a low salt content. The washed hydrogel may be milled to the desired size, or otherwise dried, ultimately to the point where its structure no longer changes as a result of shrinkage. When preparing such synthetic silicas, the objective is to obtain abrasives which provide maximal cleaning (i.e. removal of stained pellicle) with minimal damage to the tooth enamel and other oral tissue.

U.S. Pat. No. 4,153,680 and GB Patent Application 2,038, 303A both disclose the general use of silica hydrogels or hydrated silica gels as dental abrasives.

U.S. Pat. No. 5,939,051 discloses dentifrice compositions prepared with silica gels having low abrasion and high cleaning properties.

U.S. Pat. Nos. 5,658,553 and 5,651,958 disclose dentifrice compositions containing a combination of precipitated silica and silica gels having high cleaning and low abrasion as indicated by their low radioactive dentin abrasion (RDA) values.

Copending patent application U.S. Ser. No. 09/567,402 filed May 9, 2000 discloses a silica hydrogel containing about 10 to about 35% by weight water, whereby the dentifrice composition has an RDA of from 110 to 200, and a PCR of from about 150 to about 300.

In spite of the extensive prior art relating to silica hydrogels and other abrasive compounds used to prepare dentifrice compositions for oral cleaning and stain removal, there is still a need for additional compositions providing improved pellicle cleaning and stain removal.

SUMMARY OF THE INVENTION

In accordance with the present invention there is provided a silica abrasive dentifrice composition which exhibits heightened tooth stain removal which composition comprises an orally acceptable vehicle containing a combination of a low oil absorption silica abrasive having an oil absorption value of less than 100 cubic centimeters (cc)/100 grams (g) silica and a proteolytic enzyme.

DETAILED DESCRIPTION OF THE INVENTION

Low Oil Absorption Silica Abrasives

Silica abrasives useful in the practice of the present invention include silica gels and precipitated amorphous silica having an oil absorption value of less than 100 cc/100 g silica and preferably in the range of from about 45 cc/100 g to less than about 70 cc/100 g silica. These silicas are colloidal particles having an average particle size ranging from about 3 microns to about 12 microns, and more preferably between about 5 to about 10 microns and a pH range from 4 to 10 preferably 6 to 9 when measured as a 5% by weight slurry.

Oil absorption values are measured using the ASTM Rub-Out Method D281. The low oil absorption silica abrasive is present in the oral are compositions of the present invention at a concentration of about 5 to about 40% by weight and preferably about 10 to about 30% by weight.

Low oil absorption silica abrasives particularly useful in the practice of the present invention are marketed under the trade designation Sylodent XWA by Davison Chemical Division of W. R. Grace & Co., Baltimore, Md. 21203. Sylodent 650 XWA, a silica hydrogel composed of particles of colloidal silica having a water content of 29% by weight averaging from about 7 to about 10 microns in diameter, and an oil absorption of less than 70 cc/100 g of silica is a preferred example of a low oil absorption silica abrasive useful in the practice of the present invention.

Another low oil absorption silica abrasive particularly useful in the practice of the present invention is marketed under the trade designation DP-105 by J. M. Huber Chemicals Division, Havre de Grace, Md. 21078 is a precipitated amorphous silica having an average particle size distribution from 5 to 12 microns and an oil absorption in the range of 50 to 70 cc/100 g.

The low oil absorption silica abrasive can be used as the sole abrasive in preparing the dentifrice composition of the present invention or in combination with other known dentifrice abrasives or polishing agents.

Commercially available abrasives which may be used in combination with the low oil absorption silica abrasive include precipitated silicas having a mean particle size of up to about 20 microns, such as Zeodent 115, marketed by J. M. Huber Chemicals Division, Havre de Grace, Md. 21078, or Sylodent 783 marketed by Davison Chemical Division of W. R. Grace & Company. Other useful dentifrice abrasives include sodium metaphosphate, potassium metaphosphate, tricalcium phosphate, dihydrated dicalcium phosphate, aluminum silicate, calcined alumina, bentonite or other siliceous materials, or combinations thereof.

The total quantity of abrasive present in the dentifrice compositions of the present invention is at a level of from about 5% to about 40% by weight, preferably from about 5% to about 30% by weight when the dentifrice composition is a toothpaste.

Enzymes

The proteolytic enzymes useful in the practice of the present invention are those well known protein substances within the class of proteases, which breakdown or hydrolyze proteins (proteases). The proteolytic enzymes are obtained from natural sources or by the action of microorganisms having a nitrogen source and a carbon source. Examples of proteolylic enzymes useful in the practice of the present invention include papain, bromelain, chymotrypsin, ficin and alcalase.

Papain obtained from the milky latex of the Papaya tree is the proteolytic enzyme preferred for use in the practice of the present invention and is incorporated in the oral care composition of the present invention in an amount of about 0.1 to about 10% by weight and preferably about 0.5 to about 5% by weight, such papain having an activity of 150 to 300 units per milligram as determined by the Milk Clot Assay Test of the Biddle Sawyer Group (see J. Biol. Chem., vol. 121, pages 737–745).

Enzymes which may beneficially be used in combination with the proteolytic enzymes include carbohydrases such as glucoamylase, alpha-amylase, beta-amylase, dextranase and mutanase and lipases such as plant lipase, gastric lipase and pancreatic lipase.

Glucoamylase is a saccharifying glucoamylase of Aspergillus niger origin. This enzyme can hydrolyze both the alpha-D-1,6 glucosidic branch points and the alpha-1,4 glucosidic bonds of glucosyl oligosaccharides. The product of this invention comprises about 0.001 to 10% of the carbohydrases. The lipase enzyme used in this invention is derived from a select strain of Aspergillus niger. The enzyme has maximum lipolytic activity at pH 5.0 to 7.0 when assayed with olive oil. The enzyme has 120,000 lipase units per gram.

The carbohydrases and lipases may be included in the dentifrice composition at a concentration of about 0.10 to about 5.0% by weight and preferably about 0.2 to about 2% by weight. Among the carbohydrases useful in accordance with this invention are glucoamylase, alpha and beta-amylase, dextranase and mutanase.

Dentifrice Vehicle

The orally-acceptable dentifrice vehicle used to prepare the dentifrice composition comprises a water-phase, containing a humectant therein. The humectant is preferably glycerin, sorbitol, xylitol, and/or propylene glycol of molecular weight in the range of 200 to 1,000; but, other humectants and mixtures thereof may also be employed. The humectant concentration typically totals about 5 to about 70% by weight of the oral composition.

Reference hereto to sorbitol refers to the material typically commercially available as a 70% aqueous solution. Water is present typically in amount of at least about 10% by weight, and generally about 25 to 70% by weight of the oral composition. Water employed in the preparation of commercially suitable toothpastes should preferably be deionized and free of organic impurities. These amounts of water include the free water which is added plus that which is introduced with other materials such as with sorbitol.

The dentifrice compositions of the present invention can contain a variety of optional dentifrice ingredients. As described below, such optional ingredients can include, but are not limited to, thickening agents, surfactants, a source of fluoride ions, a synthetic anionic polycarboxylate, a flavoring agent, antibacterial agents, antitartar and coloring agents.

Thickening Agents

Thickeners used in the compositions of the present invention include natural and synthetic gums and colloids. Not all naturally occurring polymer thickeners (such as cellulose or carrageenans) are compatible with dentifrice ingredients (specifically enzymes) of dentifrice compositions when formulated in the presence of proteolytic enzymes. Thickeners compatible with proteolytic enzymes include xanthan gum, polyglycols of varying molecular weights sold under the tradename Polyox , and polyvinylpyrrolidone. Compatible inorganic thickeners include amorphous silica compounds which function as thickening agents and include colloidal silicas compounds available under the trade designation Cab-o-sil manufactured by Cabot Corporation and distributed by Lenape Chemical, Bound Brook, N.J.; Zeodent 165 from J. M. Huber Chemicals Division, Havre de Grace, Md. 21078; and Sylodent 15, available from Davison Chemical Division of W. R. Grace Corporation, Baltimore, Md. 21203. Other inorganic thickeners include natural and synthetic clays, lithium magnesium silicate (laponite) and magnesium aluminum silicate (Veegum).

The thickening agent is present in the dentifrice composition in amounts of about 0.1 to about 10% by weight, preferably about 0.5 to about 4.0% by weight.

Surfactants

Surfactants are used in the compositions of the present invention to achieve increased prophylactic action and render the dentifrice compositions more cosmetically acceptable. The surfactant is preferably a detersive material which imparts to the composition detersive and foaming properties.

Anionic surfactants such as higher alkyl sulfates such as sodium lauryl sulfate are not compatible with enzymes. Anionic surfactants facilitate denaturing of the enzyme and loss in activity. As a result, it is important to the practice of the present invention to use a surfactant or combination of surfactants that are compatible with the enzymes present in the toothpaste formulation and provide the requisite foaming characteristics. Examples of enzyme compatible surfactants include nonanionic polyoxyethylene surfactants such as Polyoxamer 407, Steareth 30, Polysorbate 20, and PEG-40 castor oil and amphoteric surfactants such as cocamidopropyl betaine and cocamidopropyl betaine lauryl glucoside. Preferred surfactants include a combination of Polyoxamer 407, polysorbate 20, PEG-40 castor oil and cocamidopropyl betaine at a total surfactant concentration in the dentifrice composition of between about 2 to about 10% by weight and preferably between about 3.5 to about 6.5% by weight at weight ratios of 2.5 Polyaxomer 407, 2.5 PEG-40 castor oil, 3.3 Polysorbate-20 and 1.0 cocamidopropyl betaine.

Fluoride and Other Active Agents

The dentifrice composition of the present invention may also contain a source of fluoride ions or fluorine-providing component, as anticaries agent in amount sufficient to supply about 25 ppm to 5,000 ppm of fluoride ions and include inorganic fluoride salts, such as soluble alkali metal salts. For example, preferred fluoride sources which are compatible with enzymes present in the composition are sodium fluoride, potassium fluoride, sodium fluorosilicate, ammonium fluorosilicate, as well as tin fluorides, such as stannous fluoride and stannous chloride. Sodium fluoride is preferred.

In addition to fluoride compounds, there may also be included antitartar agents such as pyrophosphate salts including dialkali or tetraalkali metal pyrophosphate salts such as $Na_4P_2O_7$, $K_4P_2O_7$, $Na_2K_2P_2O_7$, $Na_2H_2P_2O_7$ and $K_2H_2P_2O_7$ long chain polyphosphates such as sodium hexametaphosphate and cyclic phosphates such as sodium trimetaphosphate. These antitartar agents are included in the dentifrice composition at a concentration of about 1 to about 5% by weight.

Another active agent useful in dentifrice compositions of the present invention are antibacterial agents, which can be from 0.2 to 1.0% by weight of the dentifrice composition. Such useful antibacterial agents include non-cationic antibacterial agents which are based on phenolic or bisphenolic compounds, such as halogenated diphenyl ethers such as Triclosan (2,4,4'-trichloro-2'-hydroxydiphenyl ether).

Enzyme Stabilizing Agents

The dentifrice composition of the present invention may also contain ingredients which stabilize enzymes in a dentifrice environment. These stabilizers protect the enzyme from inactivation by chelating metal impurities present in the dentifrice composition which have the propensity to denature the active site of the enzyme by protecting the enzyme from oxidation. Chelating agents include, ethylene diamine tetraacetic acid (EDTA) and sodium gluconate at concentrations between 0.01 and 1%, preferably between 0.1 and 0.5%. Agents stabilizing the enzyme against oxidation include sodium bisulfite, metal gallates, sodium stannate and ascorbic acid at concentrations between about 0.1 and about 1.5%, preferably between about 0.3 and about 0.75%.

Anionic Polycarboxylate

Synthetic anionic polycarboxylates may also be used in the dentifrice compositions of the present invention as an efficacy enhancing agent for any antibacterial, antitartar or other active agent within the dentifrice composition. Such anionic polycarboxylates are generally employed in the form of their free acids or preferably partially or more preferably fully neutralized water soluble alkali metal (e.g. potassium and preferably sodium) or ammonium salts. Preferred are 1:4 to 4:1 copolymers of maleic anhydride or acid with another polymerizable ethylenically unsaturated monomer, preferably methylvinylether/maleic anhydride having a molecular weight (M.W.) of about 30,000 to about 1,800,000 most preferably about 30,000 to about 700,000. Examples of these copolymers are available from GAF Corporation under the tradename Gantrez, e.g. AN 139 (M.W. 500,000), AN 119 (M.W. 250,000); S-97 Pharmaceutical Grade (M.W. 700,000), AN 169 (M.W. 1,200,000–1,800,000), and AN 179 (M.W. above 1,800,000); wherein the preferred copolymer is S-97 Pharmaceutical Grade (M.W. 700,000).

When present, the anionic polycarboxylates is employed in amounts effective to achieve the desired enhancement of the efficacy of any antibacterial, antitartar or other active agent within the dentifrice composition. Generally, the anionic polycarboxylates is present within the dentifrice composition from about 0.05% to about 4% by weight, preferably from about 0.5% to about 2.5% by weight.

Flavor

The dentifrice composition of the present invention may also contain a flavoring agent. Flavoring agents which are used in the practice of the present invention include essential oils as well as various flavoring aldehydes, esters, alcohols, and similar materials. Examples of the essential oils include oils of spearmint, peppermint, wintergreen, sassafras, clove, sage, eucalyptus, marjoram, cinnamon, lemon, lime, grapefruit, and orange. Also useful are such chemicals as menthol, carvone, and anethole. Of these, the most commonly employed are the oils of peppermint and spearmint.

The flavoring agent is incorporated in the dentifrice composition at a concentration of about 0.1 to about 5% by weight and preferably about 0.5 to about 1.5% by weight.

Other Ingredients

Various other materials may be incorporated in the dentifrice compositions of this invention, including desensitizers, such as potassium nitrate; whitening agents, such as hydrogen peroxide, calcium peroxide and urea peroxide; preservatives; silicones; and chlorophyll compounds. These additives, when present, are incorporated in the dentifrice composition in amounts which do not substantially adversely affect the properties and characteristics desired.

Preparation of the Dentifrice

The preparation of dentifrices is well known in the art by reference. More specifically, to prepare a dentifrice of the present invention, generally the humectants e.g. glycerin, sorbitol, propylene glycol, and polyethylene glycol; are dispersed in the water in a conventional mixer under agitation. Into the dispersion are added the enzyme or enzymes organic thickeners, such as xanthan gum; any anionic polycarboxylate; any salts, such as sodium fluoride anticaries agents; tetrasodium pyrophosphate, sodium tripolyphosphate anticalculus salts and any sweeteners; the resultant mixture is agitated until a homogeneous gel phase is formed. Into the gel phase are added a pigment such as $TiO_2$, and any acid or base required to adjust the pH. These ingredients are mixed until a homogenous phase is obtained. The mixture is then transferred to a high speed/vacuum mixer; wherein, the inorganic silica thickener, such as Zeodent 165; and surfactant ingredients are added to the mixture. The low oil absorption silica abrasive is added at this point, along with other abrasives to be used in the composition. Any water insoluble antibacterial agent, such as Triclosan, is solubilized in the flavor oils to be included in the dentifrice and the solution is added along with the surfactants to the mixture, which is then mixed at high speed for from 5 to 30 minutes, under vacuum of from about 20 to 50 mm of Hg, preferably about 30 mm Hg. The resultant product is in each case a homogeneous, semi-solid, extrudable paste or gel product.

The following example further describes and demonstrates preferred embodiments within the scope of the present invention. The example is given solely for illustration, and are not to be construed as limitation of this invention as many variations thereof are possible without departing from its spirit and scope.

EXAMPLE 1

A series of liquid solutions were prepared using the ingredients listed in Table I below.

TABLE I

| | Weight % | | | |
|---|---|---|---|---|
| Composition No. | 1 | 2 | 3 | 4 |
| Ingredients | | | | |
| Water | 77.89 | QS | QS | QS |
| Trisodium phosphate | 1.10 | 1.1 | 1.1 | 1.1 |
| Sodium bisulfite | 0.49 | 0.5 | 0.5 | 0.5 |
| Disodium hydrogen phosphate | 0.29 | 0.29 | 0.29 | 0.29 |
| Sodium acid pyrophosphate | 0.20 | 0.2 | 0.2 | 0.2 |
| Sodium dihydrogen phosphate | 0.30 | 0.3 | 0.3 | 0.3 |
| Zeodent 115 silica abrasive* | 20 | — | 10 | 10 |
| Sylodent 650XWA silica gel** | — | 20 | 10 | 10 |
| Papain | — | 0.50 | — | 0.5 |

*Zeodent 115 is a precipitated silica abrasive having an oil absorption value of 105–110 cc/100 g silica.
**Sylodent 650XWA is a low oil absorption silica hydrogel having an oil absorption value of less than 70 cc/100 g silica Composition 1 was a placebo solution containing 20% of a Zeodent 115, a silica abrasive outside the scope of the present invention buffered to maintain the pH of the solution at pH 7, Composition 2 was a comparative solution containing the low oil absorption silica abrasive Sylodent 650XWA. Composition 3 contained a mixture of Zeodent 115 silica abrasive and the low oil absorption silica abrasive Sylodent 650XWA but without the enzyme papain being present. Composition 4 contained both the low oil absorption silica Sylodent XWA650 silica abrasive, the Zeodent 115 abrasive and the enzyme papain.

Compositions 1 to 4 were tested for stain removal efficacy. In a series of brushing tests extracted bovine molars having a high degree of discoloration were soaked in Compositions 1 to 4 for 2 hours at ambient temperature followed by brushing 25 and/or 50 strokes with Compositions 1 to 4 using a V-8 cross brushing machine to determine the stain removal properties of the dentifrice compositions. Before the discolored teeth were exposed to Compositions 1 to 4, the color of the teeth was measured with a Gardner tristiulus calorimeter using values obtained from CIE L*, a* and B* scale. This scale represents the mathematical approximation of the non-linear response of the eye to light.

A zero value for a* and b* means some shade of gray. Positive values for a* and b* indicate redness and yellowness. Negative a* and b* represents values for green and blue. After treatment with Compositions 1 to 4, the color of the teeth was again measured. The level of stain removal is calculated using the equation $\Lambda E=\sqrt{((\Lambda L^*)^2+(\Lambda a^*)2+(\Lambda b^*)2)}$ where $\Lambda E$ represents an increase in whiteness that is, the higher the value of $\Lambda E$, the greater the tooth stain removal effected by the brushing. $\Lambda L^*$, $\Lambda a^*$ and $\Lambda b^*$ represent the changes that have occurred in these parameters after the treatment. The $\Lambda E$ values are recorded in Table II below.

TABLE II

| Composition | ΛE After Initial Soaking | ΛE After Brushing 25X | ΛE After Brushing 50X |
|---|---|---|---|
| 1 | 3.99 | 8.39 | 9.37 |
| 2 | 1.38 | 11.30 | 15.41 |
| 3 | 6.46 | 9.71 | 11.26 |
| 4 | 9.89 | 14.40 | 16.24 |

The data recorded in Table II demonstrate that the composition of the present invention (Composition 4) effects superior stain removal, especially when compared to comparative Compositions 2 and 3, thereby demonstrating the improved efficacy in stain removal attainable with the combination of a low oil absorption silica abrasive and a proteolytic enzyme such as papain.

EXAMPLE II

The procedure of Example 1 was repeated except that one composition (Composition A) was prepared using a mixture of the enzymes papain, lipase and glycoamylase and silica abrasives Zeodent 115 and Sylodent 650XWA. A second composition (Composition B) was prepared similar to Composition A except the enzyme lipase was not included in the composition. For purposes of comparison, a third composition (Composition C) was prepared which did not contain any enzyme.

TABLE III

| | Weight % | | |
|---|---|---|---|
| Composition No. | A | B | C |
| Ingredients | | | |
| Water | QS | QS | QS |
| Glycerine | 30.0 | 30.0 | 30.0 |
| Sorbitol | 30.0 | 30.0 | 30.0 |
| Trisodium phosphate | 1.1 | 1.1 | 1.10 |
| Sodium bisulfite | 0.5 | 0.5 | 0.49 |
| Disodium hydrogen phosphate | 0.29 | 0.29 | 0.29 |
| Sodium acid pyrophosphate | 0.2 | 0.2 | 0.20 |
| Sodium dihydrogen phosphate | 0.3 | 0.3 | 0.30 |
| Zeodent 115 | 0.0 | 10.0 | 10.0 |
| Sylodent 650XWA | 10 | 10.0 | 10.0 |
| Papain | 0.50 | 0.50 | — |
| Lipase | 0.2 | — | — |
| Glucoamylase | 0.30 | 0.30 | — |

Stained bovine teeth were soaked in Compositions A, B and C and brushed for 100 strokes. The cumulative change in the degree of brightness, $\Lambda E$, is recorded in the Table IV below.

TABLE IV

| Composition | ΛE |
|---|---|
| A | 16.1 |
| B | 11.5 |
| C | 9.6 |

Reference to Table IV indicate that the level of tooth stain removal was highest when a mixture of three enzymes were present in the composition (Composition A). Stain removal was lower when only two enzymes were present (Composition B). However, both Compositions A and B exhibited significantly higher tooth stain removal when compared to Composition C which did not contain any enzymes.

EXAMPLE III

An example of a dentifrice composition prepared in accordance with the present invention is set forth in Table V below.

TABLE V

| Ingredient | Weight % |
|---|---|
| Water | 15.5 |
| Polyoxamer 407 | 1.5 |
| Glycerine | 26 |
| Tetrasodium pyrophosphate | 2.0 |
| Sodium tripolyphosphate | 3.0 |
| Xanthan gum | 0.85 |
| NaF | 0.243 |
| Na saccharin | 0.40 |
| NaH$_2$PO$_4$ | 0.30 |
| Na$_2$HPO$_4$ | 0.23 |
| NaHSO$_3$ | 0.10 |
| Sorbitol | QS |
| Sylodent 650XWA | 20 |
| Thickening silica | 1.5 |
| TiO$_2$ | 0.40 |
| PEG-600 | 4.0 |
| PG-40 castor oil | 1.55 |
| PEO polyox | 0.35 |
| Papain | 0.50 |
| Glucoamylase | 0.10 |
| Flavor | 1.3 |
| Polysorbate 20 | 2.0 |
| Tego betaine ZF (30% solution) | 2.0 |

EXAMPLE IV

The level of papain enzyme activity and bioavailability over a 14 week period was monitored and measured in a dentifrice composition formulated with a low oil absorption abrasive Sylodent 650XWA and a mixture of enzymes (papain and glucoamylase). Table VI depicts the composition of the toothpaste formulated with the low oil absorption abrasive.

TABLE VI

| Ingredient | Weight % |
|---|---|
| Water | 15.5 |
| Pluronic F-127 | 4.0 |
| Glycerine | 26 |
| Tetrasodium pyrophosphate | 2.0 |
| Sodium tripolyphosphate | 3.0 |
| Xanthan gum | 0.85 |
| NaF | 0.243 |
| Na saccharin | 0.40 |
| $NaH_2PO_4$ | 0.30 |
| $Na_2HPO_4$ | 0.23 |
| $NaHSO_3$ | 0.10 |
| Sorbitol | QS |
| Sylodent 650XWA | 20 |
| Pigment | 0.40 |
| PEG-600 | 3.0 |
| PG-40 castor oil | 3.75 |
| PVP | 3.0 |
| Papain | 0.50 |
| Glucoamylase | 0.10 |
| Flavor | 1.0 |
| Tego betaine ZF (30% solution) | 2.0 |

Aging Test

At specific intervals over the 14 week aging period, toothpaste samples were removed from constant room temperature aging room maintained at 25° C. and the activity of the papain enzymes was measured by titration. The activity of papain was determined using a standard titration method (Methods in Enzymology, vol. XIX, p. 226, 1970) which measures the amount of acid produced during the hydrolysis of bezoyl-L-argininine ethyl ester (BAEE) by the enzyme. One unit of active papain enzyme will hydrolyze one micromol of BAEE per minute at 25 deg. C. and pH 6.2 under the specified conditions.

For purposes of comparison the procedure of Example IV was repeated in which a silica abrasive which had an oil absorption value of greater than 100 cc/g (Zeodent 115) was substituted for the low oil absorption silica abrasive Slyodent 650XWA. The level of enzyme activity expressed as percent is recorded for papain in Table VI below.

TABLE VI

| | Relative papain enzyme activity (%) at room temperature | |
|---|---|---|
| Time (weeks) | Zeodent 115 Abrasive | Sylodent 650XWA) |
| 0 | 100 | 100 |
| 3 | 68 | 91 |
| 9 | 31 | 86 |
| 14 | 18 | 82 |

The results recorded in Table VI indicate that the stability of papain in the dentifrice containing the low oil absorption abrasive Sylodent 650XWA (less than 70 cc/100 g silica) is significantly greater over a 14 week aging period as compared to a similar dentifrice prepared with a silica abrasive (Zeodent 115) having an oil absorption greater than 100 cc/100 g silica (105–110 cc/100 g silica).

What is claimed is:

1. An abrasive dentifrice composition which effects enhanced tooth and stain removal which comprises an orally acceptable vehicle containing an effective amount of a combination of a silica abrasive having an oil absorption value less than 100 cc/100 g silica and a proteolytic enzyme.

2. The composition of claim 1 wherein the silica abrasive has an oil absorption value less than 70 cc/g silica.

3. The composition of claim 1 wherein the low oil absorption silica abrasive is present in the composition at a concentration of about 5 to about 40% by weight of the composition.

4. The composition of claim 1 wherein the proteolytic enzyme is papain.

5. The composition of claim 1 wherein the papain is present in the composition at a concentration of about 0.1 to about 5.0% by weight of the composition.

6. The composition of claim 1 wherein the proteolytic enzyme is present in the dentifrice in combination with a lipase.

7. The composition of claim 1 wherein the proteolytic enzyme is present in the dentifrice composition in combination with a lipase and glucoamylas.

8. A method for effecting enhanced tooth stain removal which comprises preparing a dentifrice comprised of an orally acceptable vehicle containing an effective amount of a combination of a silica abrasive having an oil absorption value less than 100 cc/100 g silica and at least a proteolytic enzyme and then applying said dentifrice to tooth stains.

9. The method of claim 8 wherein the silica abrasive has an oil absorption value less than 70 cc/100 g silica.

10. The method of claim 8 wherein the low oil absorption silica abrasive is present in the dentifrice at a concentration of about 5 to about 40% by weight of the dentifrice.

11. The method of claim 8 wherein the proteolytic enzyme is papain.

12. The composition of claim 1 wherein the proteolytic enzyme is present in the dentifrice in combination with a lipase and glycoamylase.

13. The method of claim 8 wherein the proteolytic enzyme is present in the dentifrice in combination with a lipase.

14. The method of claim 8 wherein the proteolytic enzyme is present in the dentifrice composition in combination with a lipase and carbohydrase.

* * * * *